United States Patent

Agnus et al.

[11] Patent Number: 6,123,930
[45] Date of Patent: Sep. 26, 2000

[54] COMPOSITION FOR THE TREATMENT OF THE NAILS, CONTAINING A SULPHUR-BEARING AMINOACID

[75] Inventors: Dominique E Agnus, La Varenne Saint Hilaire; Jean-Claude Ser, Chevilly-Larue, both of France

[73] Assignee: L'Oreal, Paris, France

[21] Appl. No.: 08/911,280

[22] Filed: Aug. 14, 1997

Related U.S. Application Data

[63] Continuation of application No. 07/951,763, Sep. 25, 1992, abandoned.

[30] Foreign Application Priority Data

Sep. 26, 1991 [FR] France ..................... 91 11842

[51] Int. Cl.[7] ......................................... A61K 7/04
[52] U.S. Cl. ............................................. 424/61; 424/401
[58] Field of Search ........................................ 424/61, 401

[56] References Cited

U.S. PATENT DOCUMENTS

| | | | |
|---|---|---|---|
| 4,381,294 | 4/1983 | Bouillon | 424/61 |
| 4,710,376 | 12/1987 | Evans | 514/2 |
| 4,935,230 | 6/1990 | Naito | 424/71 |
| 5,047,249 | 9/1991 | Rothman | 514/886 |

FOREIGN PATENT DOCUMENTS 3111 of 1965 France.

OTHER PUBLICATIONS

Szyrle et al "Vibratory cleaning of nails after mechanical working" Fichier Chemical Abstracts vol. 114, No. 6 Abstract No. 47427g.

WPI, Week 7841, Abstract No. 78–73629A.

French Search Report—FR 91 11842.

*Primary Examiner*—Carlos A. Azpuru
*Attorney, Agent, or Firm*—Nixon & Vanderhye PC

[57] ABSTRACT

Composition for the treatment of the nails, containing a sulphur-bearing aminoacid or derivative thereof. This composition is prepared by introducing a sulphur-bearing aminoacid together with sodium tetraborate into an aqueous or water-alcohol medium. The combination of these two ingredients gives a composition with which embrittled or damaged nails can be treated and at the same time cuticles can be eliminated.

9 Claims, No Drawings

COMPOSITION FOR THE TREATMENT OF THE NAILS, CONTAINING A SULPHUR-BEARING AMINOACID

This application is a continuation of U.S. Ser. No. 07/951,763, filed Sep. 25, 1992, now abandonded, which is a continuation of French Patent No. 9,111,842 filed Sep. 26, 1991.

The present invention concerns a composition for the treatment of the nails, containing a sulphur-bearing aminoacid.

It is known that sulphur-bearing aminoacids, in particular S-carboxymethylcysteine, play an important part in the process of keratinization during the formation of the nails, and can consequently be used for the treatment of damaged and embrittled nails to harden and thicken them and to improve their appearance.

In the special French medical patent 3111M a treatment is described for the nails, involving a medicament, specifically a cream, containing S-carboxymethylcysteine.

FR-A 1603 describes the use for the care of hair and nails, of acylmethionines in which the acyl group is $C_6$ to $C_{22}$.

FR-A 2503151 describes the use for the treatment of the nails, of cystine or cysteine derivatives with a butyryl group substituted on the amine function.

Furthermore, it is generally known that sodium tetraborate can be used as a base for the neutralization of acids.

The subject of the present invention is a composition for the treatment of the nails, containing a sulphur-bearing aminoacid or derivative thereof, characterized in that it is prepared by introducing a sulphur-bearing aminoacid into an aqueous or water-alcohol medium together with sodium tetraborate.

It has been shown that in such a composition the sodium tetraborate has two functions:
1) It neutralizes the sulphur-bearing aminoacid, forming its sodium salt. When the sulphur-bearing aminoacid is not soluble in cold water, as in the case of S-carboxymethylcysteine, this neutralization allows it to become solubilized.
2) It has a buffering effect, which enables the solution obtained to be maintained at a pH close to 7.5. This is high enough to allow softening and swelling of the cuticles, but low enough to avoid attack on the skin and flesh surrounding the nail.

Consequently, the composition conforming to the invention allows both the treatment of the nails to prevent their embrittlement or softening, and the treatment of the cuticles to facilitate their elimination.

The medium in which the sulphur-bearing aminoacid and the sodium tetraborate are dissolved in conformity with the invention is an aqueous or water-alcohol medium. In the latter case the alcohol used is preferably a monoalcohol with $C_1$–$C_3$. For preference, the proportion of alcohol ranges from 0 to 35% by weight relative to the aqueous medium.

For preference, the sulphur-bearing aminoacid is chosen from the group formed by methionine, cysteine, S-carboxymethylcysteine and their derivatives. Among this group S-carboxymethylcysteine is preferred.

For preference, the sulphur-bearing aminoacid is introduced into the composition in a proportion ranging from 0.5 to 5% by weight relative to the total weight of the composition, and the sodium tetraborate is introduced in a proportion of 0.5 to 5% by weight relative to the total weight of the composition. The sulphur-bearing aminoacid/sodium tetraborate weight ratio is between 2 and 0.5, preferably between 1 and 0.5.

The compositions conforming to the invention may contain water-soluble cosmetic and/or pharmaceutical active ingredients. Among such active ingredients the following can be mentioned:

polyhydric alcohols such as glycerine, ethylene glycol, propane diol-1,2 and erythritol, non-sulphur-bearing aminoacids such as proline, arginine, lysine, histidine, hydroxyproline, and their derivatives, antifungal, antiseptic and antimicrobial agents such as benzalkonium chloride or benzethonium chloride, chlorhexidine, and the derivatives of pyridinethione in acid form, more especially those marketed under the trade name "OMADINE" by the company OLIN CHEMICALS, and vitamins, for example panthenol and vitamin H.

One may also introduce a cosmetically and/or pharmaceutically acceptable adjuvant selected from the group formed by:

texturing or thickening agents such as the hydroxyalkylcelluloses, the acrylic homopolymers or copolymers, the xanthane gums, tragacanth gum, gum arabic, and the vinylpyrrolidone/vinylacetate copolymers;

preservatives such as methyl or butyl parahydroxybenzoate;

colourants such as FD & C yellow No. 5, FD & C red No. 4, FD & C blue No. 1, D & C green No. 5, FD & C green No. 3, D & C red No. 33, FD & C red No. 40, D & C yellow No. 10, D & C violet NO. 2;

perfumes, and

UV filters.

To treat the nails and the cuticles, the user can either immerse the tips of the fingers in a container containing the composition conforming to the invention, or apply the composition to the nails and cuticles using a brush or any other suitable applicator.

The examples given below, which are purely illustrative and not limitative, are intended to explain the invention more clearly.

EXAMPLE 1

A composition having the following formulation by weight was prepared by introducing the various ingredients into water:

| | |
|---|---:|
| S-carboxymethylcysteine | 1 g |
| Sodium tetraborate | 2 g |
| Ethanol | 20 g |
| Glycerine | 5 g |
| Methyl parahydroxybenzoate | 0.5 g |
| Acrylic polymer | 0.5 g |
| Water | made up to 100 g |

It was found that a single application of the composition obtained by immersing the tips of the fingers for 5 min allowed easy elimination of the cuticles, and that if this application was repeated twice a week for two months, the appearance of the nails was very clearly improved and the nails became harder and less brittle.

EXAMPLE 2

As in example 1, a composition was prepared having the following formulation by weight:

| | |
|---|---:|
| S-carboxymethylcysteine | 5 g |
| Sodium tetraborate | 5 g |
| Polyvinylpyrrolidone | 0.3 g |
| Xanthane gum | 0.5 g |
| Methyl parahydroxybenzoate | 0.5 g |
| Arginine pyrrolidone carboxylate | 1 g |
| Water | made up to 100 g |

The findings were the same as with the composition of example 1.

EXAMPLE 3

As in example 1, a composition was prepared having the following formulation by weight:

| | |
|---|---:|
| S-carboxymethylcysteine | 2 g |
| Sodium tetraborate | 4 g |
| Ethanol | 30 g |
| Hydroxyalkylcellulose | 0.6 g |
| Vinylpyrrolidone/vinyl acetate copolymer | 0.3 g |
| D-panthenol | 3 g |
| D & C red No. 33 | 0.0004 g |
| Water | made up to 100 g |

The findings were the same as with the composition of example 1.

We claim:

1. A composition for the treatment of nails to increase their hardness and to prevent their embrittlement or softening and for the treatment of cuticles to facilitate their removal, said composition comprising in an aqueous medium or medium containing water and alcohol, in an amount effective for the said treatment of said nails and cuticles, a combination of a compound selected from the group consisting of methionine, cysteine, and S-carboxymethylcysteine and sodium tetraborate, said composition having a pH 7.5 so as to soften and swell the cuticles while avoiding attack on the skin and flesh surrounding the nail.

2. The composition of claim 1 wherein said alcohol is a monoalcohol containing 1–3 carbon atoms.

3. The composition of claim 1 wherein said alcohol is present in an amount ranging from 0 to 35 percent by weight based on the weight of said medium.

4. The composition of claim 1 wherein said sulfur-bearing amino acid is present in an amount ranging from 0.5 to 5 percent by weight based on the total weight of said composition and said sodium tetraborate is present in an amount ranging from 0.5 to 5 percent by weight based on the total weight of said composition, the sulfur-bearing amino acid/ sodium tetraborate weight ratio being between 2 and 0.5.

5. The composition of claim 4 in the sulfur-bearing amino acid/sodium tetraborate weight ratio is between 1 and 0.5.

6. The composition of claim 1 which also includes a water-soluble cosmetic or pharmaceutically active ingredient or both.

7. The composition of claim 6 wherein said water-soluble active ingredient is selected from the group consisting of a polyhydric alcohol, a non-sulfur-bearing amino acid, an antifungal agent, an antiseptic agent, an antimicrobial agent and a vitamin.

8. The composition of claim 1 which also includes a water-soluble cosmetically or pharmaceutically acceptable adjuvant, or both.

9. The composition of claim 8 wherein said adjuvant is selected from the group consisting of a texturing agent, a colorant, a perfume and a U.V. filter.

* * * * *